July 7, 1959 A. DRAGHI Re. 24,666

TAMPON

Original Filed Dec. 5, 1955 2 Sheets-Sheet 1

INVENTOR
André Draghi
BY
Curtis Morris & Safford
ATTORNEYS

TAMPON

Original Filed Dec. 5, 1955 2 Sheets-Sheet 2

INVENTOR
Andre Draghi
BY
Curtis Morris & Safford
ATTORNEYS

United States Patent Office

Re. 24,666
Reissued July 7, 1959

24,666

TAMPON

André Draghi, Stamford, Conn.

Original No. 2,844,150, dated July 22, 1958, Serial No. 550,981, December 5, 1955. Application for reissue March 16, 1959, Serial No. 799,828

3 Claims. (Cl. 128—285)

Matter enclosed in heavy brackets [ ] appears in the original patent but forms no part of this reissue specification; matter printed in italics indicates the additions made by reissue.

This invention relates to a tampon for detection of cancer. More particularly it relates to a tampon as a means for mass screening and detection of cancer of the pelvic region.

The frequency of advanced cancer of the pelvic region presents to the medical profession a disturbing picture. One author states that only a relatively small percentage of the cases of cancer of the cervix is detected in the early stage of the disease. This is in spite of the various methods to detect cancer of the cervix which have been developed and are being used by gynecologists today. Among the practical barriers to prompt diagnosis is the inability and the reluctance of many women to present themselves periodically to a physician for a gynecological examination whereby early evidence of cancer may be detected; this inability and reluctance is a direct cause of the high percentage of advanced cancer which occurs or develops in the pelvic region and particularly in the region of the cervix uteri. Furthermore the protracted gynecological examination of the patient which is necessary to obtain full diognostic information, is time consuming for the physician and nurse and accordingly any such routine periodical examination may be prohibitively expensive for the patient, and the medical organization undertaking it.

Complete diagnosis to determine whether and to what extent one has cancer must require a thorough gynecological and pelvic examination and biopsy. Preliminiary diagnosis to determine if there are present any indicia of cancer however, may be asserted by taking a sample of cells which are present in the cervical canal and the vagina and the subsequent microscopic analysis of these cells. While a thorough gynecological examination and biopsy should be performed in those cases in which the preliminary diagnosis indicates cancer, the preliminary diagnosis can serve to screen many women and thus initiate the early treatment of those who have indications of cancer.

It is therefore an object of this invention to provide a means for mass screening for cytological detection of carcinomas of the pelvic region.

A further object of this invention is to provide through the cooperation of the patient herself, an accurate, inexpensive means by which cells present in the pelvic region can be collected and thus screen large numbers of women thereby reducing the percentage of cases having advanced pelvic cancer.

Another object of this invention is to provide a means for sampling vaginal cells, which can be inserted by the patient herself, and will provide satisfactory smears for laboratory evaluation without the necessity for elaborate clinical facilities.

In accordance with the present invention a cancer detection tampon is inserted into the vaginal cavity in a manner like that for the well known catamenial tampon and remains therein for a time specified by the physician. The tampon is then removed by the patient and given to a nurse who makes a smear on a slide according to the method described in articles appearing in vol. 7, No. 6 of "Cancer" at pages 1182 et. seq. and 1185 et. seq. and appearing in vol. 159, No. 12 of "The Journal of the American Medical Association" at page 1177 et seq.

A better understanding of the invention may be obtained by reference to the accompanying drawings in which.

Figure 1:
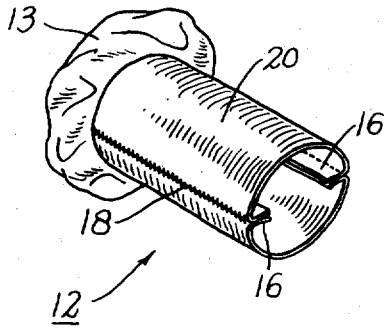
Figure 1 is a perspective view of one type of jacket according to the invention which is placed over a supporting body.
Figure 2:
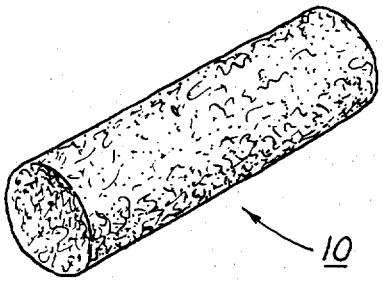
Figure 2 is a perspective view of a vaginal supporting body suitable for use with the jacket of Figure 1.

Referring to Figures 1 and 2 there is shown supporting body 10 similar in size and shape to the type generally used for catamenial tampons. Body 10 is made of a size and of a material which is sufficiently flexible to be comfortable carried in the vaginal cavity, in a preferred example this may be about ½" x 2¼". In the embodiment illustrated a cotton fiber body is employed as the supporting means and is covered by jacket 12.

Jacket 12 is formed from a piece of material sewed into a generally round tube with a closed but enlarged cap 13. Jacket 12 is made so that it covers one end and extends approximately one-half the length of body 10. The fins of material 16 along the seams 18 are on the inside of the jacket leaving the outside smooth. In the present embodiment jacket 12 is made out of a closely woven, sheer cloth which is manufactured from a non-absorbent, relatively fine, continuous filament yarn such as nylon.

Figure 3:
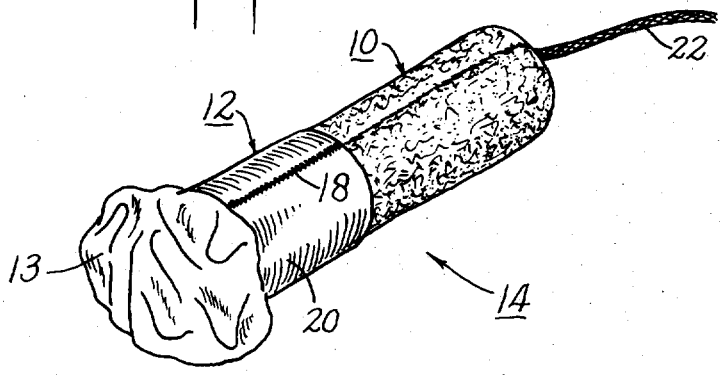
Figure 3 is a perspective view of the jacketed tampon ready for use.

Figure 3 shows body 10 and jacket 12 assembled into a detection tampon 14 which embodies features of the invention. Tampon 14 is shaped into a generally round form. One end of body 10 is covered by closed end 13 of jacket 12 and the other end is attached to a removal string 22. Removal [strip] *string* 22 is sewed into the tampon 14 by the same stitching that securely affixes jacket 12 to body 10 forming tampon 14.

Figure 4:
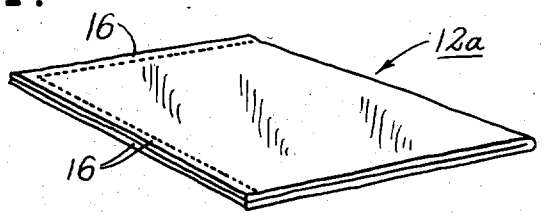
Figure 4 is a perspective view of another type of jacket suitable, according to the invention, to be assembled over a cotton pad and the assembly compressed to form the detection tampon.
Figure 5:
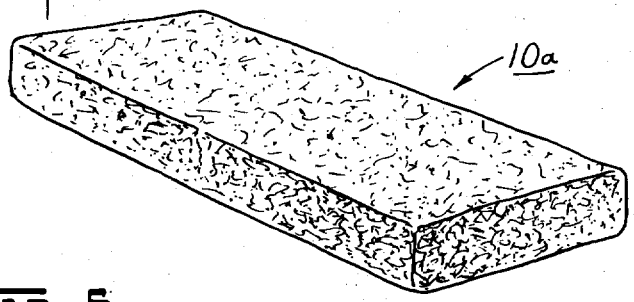
Figure 5 is a perspective view of an uncompressed cotton pad for use with the jacket of Figure 4.

Another embodiment of the invention is shown in Figures 4, 5, 6 and 7. The jacket 12a of Figure 4 is slipped over cotton pad 10a shown in Figure 5. The jacket 12a is similar to jacket 12 shown in Figure 1. Jacket 12a is a closely woven sheer cloth manufactured from relatively non-absorbent, continuous filament such as nylon. The cloth when folded back upon itself, as shown in Figure 4, is stitched along one edge extending from the fold and the edge opposite to the fold; but a very satisfactory jacket can be made from a longer and narrower piece of cloth folded back upon itself and stitched along opposite edges adjacent to the fold. Or a tubular fabric of the required width can be sewn across one end. Thus it will be seen that the [essential] feature *essentially identifying Fig. 4 with these latter alternatives* is that the jacket is closed on the sides and one end, and open at its other end and of a size adapted to contain cotton pad 10a as shown in Figure 5.

After the jacket 12a has been sewn as shown in Figure 4, it is turned inside *out* leaving a smooth exterior surface.

Figure 6:
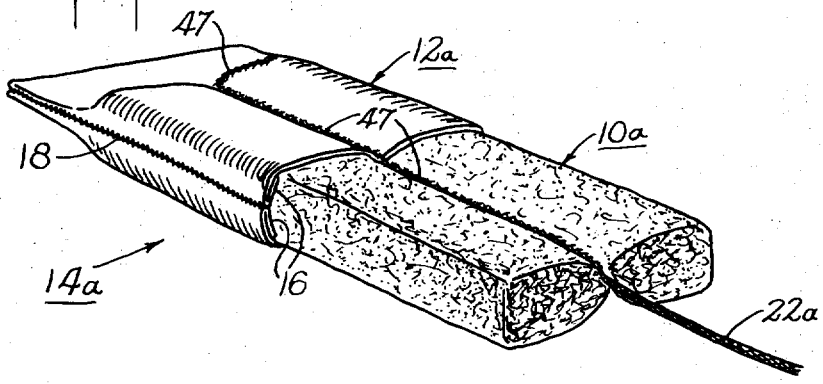
Figure 6 is a perspective view of the assembled detection tampon showing the jacket turned inside out so that the seam is on the inside and showing the jacket fitted over one end of the uncompressed cotton pad and the two sewn together with the string.

Figure 6 shows an uncompressed cotton pad 10a and jacket 12a assembled and stitched as at 47 down the center and to withdrawal cord 22a forming uncompressed tampon 14a.

Figure 7:
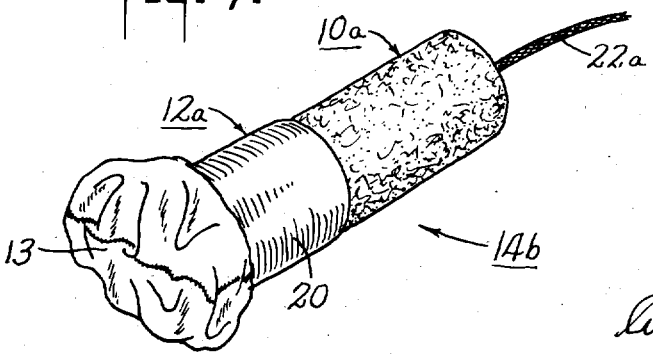
Figure 7 is a perspective view of the assembled detection tampon of Figure 6 after it has been compressed into a cylindrical form.

Figure 7 shows the assembled tampon 14b comprising jacket 12a and cotton pad 10a after the tampon has been compressed into a cylindrical shape. Surplus material at the top of the jacket forms a "chef's cap" 13a.

The jacket 12 and 12a holds whatever cells are collected from the body cavity on the surface of the jacket. Because the cloth of the jacket is non-absorbent these cells are not dehydrated and thus remain in a relatively moist condition which enables a more accurate clinical evaluation. It has also been found most satisfactory for collection of vaginal smears that the exterior surface 20 and 20a of the jacket 12 and 12a be relatively smooth. The fin of material resulting from the seam should therefore be made on the inside.

The enlarged cap 13 and 13a which extends farthest into the vaginal canal collects and retains in moist form many cells. While the specific reasons for the improved sampling through use of the enlarged cap 13 and 13a remain obscure at this time tests have proven that a large percentage of cells are collected on the cap 13 and 13a and by using a tampon with such a cap the sampling of cells from the vagina is greatly improved.

The pliability of tampons 14, 14a and 14b permits the easy removal of the collected cells by evenly smearing onto a microscope slide, with or without squeezing with finger pressure against its sides and advantageously rotating the tampon in contact with the slide.

In the embodiments I have described the tampon is comprised of a jacket of non-absorbent, relatively fine, continuous filament yarn such as nylon and a supporting body of cotton fiber. Laboratory tests have conclusively indicated that the use of the non-absorbent supporting body is also practical for the collection of cells. Thus, for the collection of cells a plastic, rubber or other non-absorbent supporting body with the nylon like jacket can be used.

I claim:

1. A vaginal type tampon comprised of a supporting body, flexible but stiff enough to project its end into the vaginal cavity and against the cervix, and a jacket secured to said body and covering one end of said supporting body and the adjacent portion of the body, but extending beyond it in a loose cap, said jacket being a fine-mesh fabric made of non-absorbent relatively fine filament.

2. A vaginal tampon comprising a jacket of relatively non-absorbent filament nylon, a body formed into a cylindrical shape, said jacket extending over said body and beyond it forming a loose cap.

3. A vaginal tampon comprising a jacket of relatively non-absorbent filament nylon and supporting means to carry said jacket, said supporting means being of a size, shape, and flexibility such that the tampon may be inserted in the vaginal cavity, and said jacket extending over said supporting means and beyond one end to form at said end a relatively large, loose cap.

References Cited in the file of this patent or the original patent

UNITED STATES PATENTS

| | | |
|---|---|---|
| 66,022 | Henderson et al. | June 25, 1867 |
| 1,555,708 | Gale | Sept. 29, 1925 |
| 2,267,030 | Hill | Dec. 23, 1941 |

OTHER REFERENCES

Brunschwig: Cancer, volume 7, pages 1182–1184, November 1954.